United States Patent [19]

Kuettner

[11] 4,176,177

[45] Nov. 27, 1979

[54] INHIBITION OF BONE RESORPTION

[75] Inventor: Klaus E. Kuettner, Chicago, Ill.

[73] Assignee: Rush-Presbyterian-St. Luke's Medical Center, Chicago, Ill.

[21] Appl. No.: 961,296

[22] Filed: Nov. 16, 1978

[51] Int. Cl.² .............. A61K 35/24; A61K 35/44; A61K 35/32
[52] U.S. Cl. .................................................. 424/95
[58] Field of Search ......................................... 424/95

[56] References Cited

U.S. PATENT DOCUMENTS 4,042,457   8/1977   Kuettner et al. .................. 195/1.8

*Primary Examiner*—Sam Rosen
*Attorney, Agent, or Firm*—Fitch, Even & Tabin

[57] ABSTRACT

A method for regulating bone resorption wherein the bone is exposed to an effective amount of a composition of matter obtained from avascular or poorly vascularized tissue by extracting the tissue with an aqueous extraction medium which includes a solute which does not irreversibly denature the proteinaceous matter to be extracted and recovering from the aqeuous extract substances having molecular weight below about 50,000.

10 Claims, 1 Drawing Figure

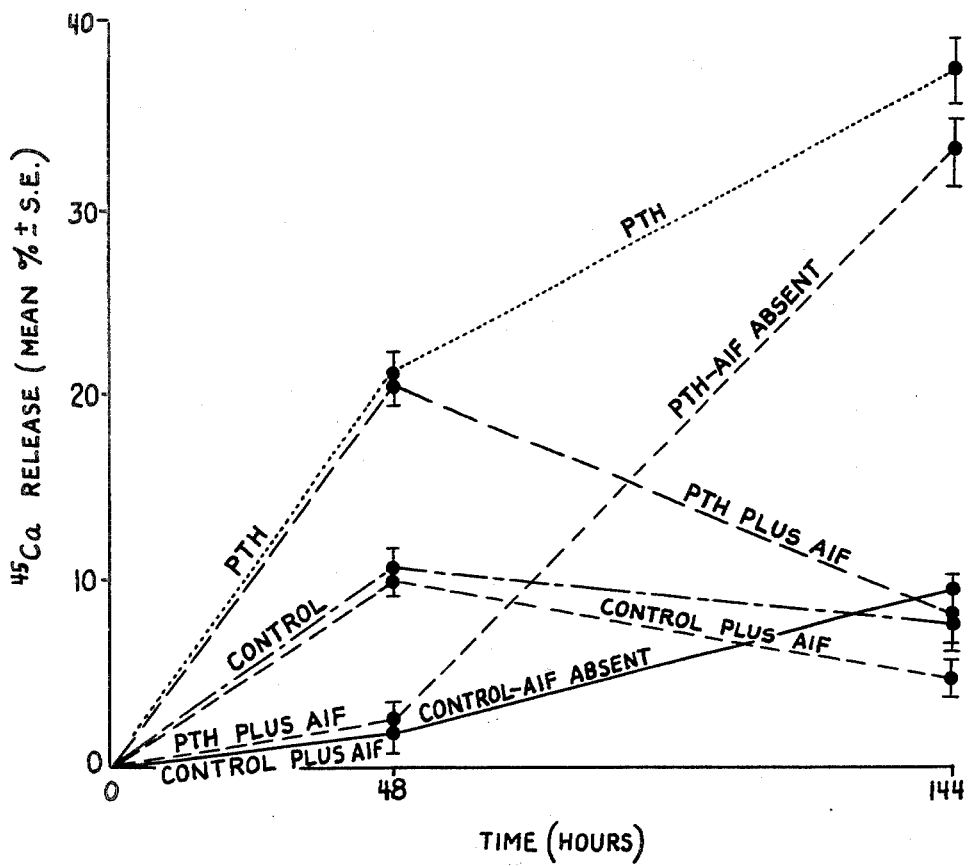
EFFECTS OF THE PRESENCE IN AND ABSENCE FROM THE CULTURE MEDIUM OF THE ANTI-INVASION FACTOR (AIF) ON PTH-STIMULATED BONE RESORPTION IN ORGAN CULTURE. VALUES ARE EXPRESSED AS THE MEAN PERCENTAGE (±STANDARD ERROR) OF $^{45}Ca$ RELEASED FROM FOUR PAIRS OF CULTURED BONES AFTER 48 AND 144 HOURS OF INCUBATION.

INHIBITION OF BONE RESORPTION

The invention described herein was made in the course of work under a grant or award from the Department of Health, Education and Welfare.

The present invention relates generally to a composition of matter having activity as an inhibitor of bone resorption, and to methods of inhibiting bone resorption utilizing the same.

Resorption of bone may be associated with various physiological events, both normal and abnormal. Examples of such normal physiological events include the growth and development of long bones, and fracture repair. Examples of such abnormal physiological events include periodontal disease, and rheumatoid arthritis. Control of bone resorption associated with such events would be highly desirable. In accordance with the present invention, inhibition of bone resorption is attained by treatment with an extract obtained from avascular or poorly vascularized tissue, such as cartilage, blood vessel walls, cornea, vitreous, lens, synovial fluid, dentin and heart valve tissue. The active component or components of the present invention are believed to have specific activity as protease and/or collagenase inhibitors. The active component or components of the present invention are further believed to reversibly inhibit the activity of osteoclasts associated with bone resorption.

The active component or components of the present invention are present in the extract disclosed in the U.S. Pat. No. 4,042,457. As set forth in that patent, avascular or poorly vascularized tissue, such as cartilage, is extracted with an aqueous extraction medium including a solute which does not irreversibly denature proteins or proteoglycans. The aqueous extract is treated so as to recover the extracted substances having a molecular weight below about 50,000. The extracted substances thus obtained will sometimes be referred to herein as "anti-invasion factor" (AIF).

U.S. Pat. No. 4,042,457 discloses the activity of that composition as an inhibitor of cell proliferation; specifically, as an inhibitor of endothelial cell growth. It has now been discovered that one or more components of the composition of that patent have activity as an inhibitor of bone resorption. It is not as yet clear whether the protein or proteins responsible for inhibition of endothelial cell proliferation are also responsible for inhibition of bone resorption, although there is some evidence that they are not.

Surprising and unexpected degree of inhibition of bone resorption by the anti-invasion factor has been obtained in vitro, as set forth hereinafter and as shown in the accompanying drawing, the single FIGURE of which comprises a graphical representation of the results thereby obtained.

Preparation of the Anti-Invasion Factor

Slices of fresh bovine nasal septa cartilage were extracted with 1 M NaCl (pH 5.8; 48 hours at 4° C.). After decantation, the NaCl concentration of the extract was raised to 3 M by adding solid NaCl. The extract was then ultrafiltered at a temperature of 4° C. on an Amicon XM-50 membrane (molecular weight cutoff 50,000) and afterward concentrated and dialyzed into physiologic saline with an Amicon UM-2 membrane (molecular weight cutoff 2,000) to yield a solution having a solids content of 5 mg/ml. The solute had a molecular weight between about 2,000 and about 50,000, was essentially free of uronic acid and hydroxyproline, and comprised about 95% protein. The solute, comprising the anti-invasion factor of the present invention, is believed to include at least four cationic proteins. After being passed through a Millipore filter (0.22 um pore size) for sterilization, portions of the resultant solution of AIF were stored frozen at $-70°$ C. until utilized.

Inhibition of Bone Resorption Utilizing the Anti-Invasion Factor

A technique for measuring bone resorption technique described by Raisz and Niemann in "Endocrinology," Volume 85, pp. 446-456 (1969) was utilized. Radioactively—labelled bone specimens were obtained by injecting a female rat in her nineteenth day of pregnancy with $^{45}Ca$, sacrificing the rat on the following day, and recovering paired shafts of the radius and ulna from the fetuses. Two culture media were provided, the first being $BGJ_b$ culture medium, available from GIBCO Corp., Grand Island, N.Y., and the second being $BGJ_b$ medium to which the above-described anti-invasion factor was added at a level of 300 ug of solids per milliliter of medium.

One set of paired bone shafts was cultured in the culture medium alone, as a control. Another set was cultured in medium to which was added parathyroid hormone (PTH) obtained from Inolex Corporation, 4221 S. Western Blvd., Chicago, Ill. at a level of 2.8 international units per milliliter of culture medium. Another set was cultured in the medium to which AIF had been added, and another set was cultured in medium to which both AIF and PTH had been added.

The cultures were maintained for 144 hours. The medium was changed every 48 hours, together with fresh additives where required. The percentage of $^{45}Ca$ released from each bone into the culture medium was used as a measure of bone resorption. The amount of $^{45}Ca$ released was determined by liquid scintillation spectrometry from the counts per minute of $^{45}Ca$ radioactivity present in the culture medium at the end of each 48-hour interval. The amount of $^{45}Ca$ remaining in each bone was also determined from the counts per minute of $^{45}Ca$ radioactivity present in the cultured bone shafts after 144 hours of culture. The sum of the counts per minute from the culture media and from the residual bone shaft provided a measure of the total $^{45}Ca$ originally present in each shaft.

The drawing shows the $^{45}Ca$ released from the paired bone shafts during the first 48 hours, as a percent of the total $^{45}Ca$ initially present, and the $^{45}Ca$ released from the paired bone shafts during the ensuing 96 hours, also as a percent of the total $^{45}Ca$ initially present. Statistical difference were analyzed by means of Student's t-test.

Bone resorption occurred in cultures to which PTH was added, whereas resorption failed to occur in bones cultured in the presence of the anti-invasion factor. Table 1 set forth the data obtained.

Table 1

Effect of the anti-invasion factor on PTH-Stimulated bone resorption in vitro. $^{45}Ca$ release is expressed as the mean ratio ± standard error of PTH-treated to untreated cultures for four pairs of fetal rat bone shafts during 144 hours of culture.

| Anti-Invasion Factor | $^{45}Ca$ release |
|---|---|
| Absent | 2.79 ± 0.19 |
| Present | 1.07 + 0.03 |

Recovery from the inhibitory effect of the AIF was achieved by transferring the bones after 48 hours of culture to medium containing PTH but not AIF (See the drawing). In fact, the percentage of $^{45}$Ca released from these explants during the subsequent 96 hours closely approximated that released from bones cultured for a total of 144 hours in the presence of PTH only. Furthermore, the effect of PTH on bone resorption during the first 48 hours was significantly diminished by adding AIF, even though fresh PTH was added at both 48 and 96 hours. The percentage of $^{45}$Ca released at the end of the culture period from these bones was not significantly different from the values obtained from control bones cultured for a total of 144 hours in medium containing neither PTH nor AIF.

These data indicate that AIF significantly suppressed PTH-stimulated bone resorption, and that the suppression could not be overcome with repeated additions of PTH to the explants. However, the action of AIF is reversible, since bones cultured for 48 hours in its presence were found equally capable of resuming PTH-stimulated resorption when transferred to medium devoid of AIF. The biologic potency of AIF was reflected in its ability to completely inhibit PTH-stimulated bone resorption which had already progressed for 48 hours.

As previously indicated, U.S. Pat. No. 4,042,457 disclosed inhibition of endothelial cell proliferation by the patented extract composition. It also disclosed the activity of the extract composition in inhibiting tissue invasion by neoplasms or inflammatory processes. It is believed that the activity of the anti-invasion factor of the present invention as an inhibitor of bone resorption is related to the activity of the extract composition of U.S. Pat. No. 4,042,457 as an inhibitor of tissue invasion.

In this connection, tissue invasion involves the interpenetration of a cell or tissue into adjacent tissues combined with the destruction of the matrix of the invaded tissue. Proliferative invasive cells elaborate proteases such as collagenase which degrades collagen, the major organic component of connective tissue matrices. The observed resistance by uncalcified cartilage to such cellular invasion may well be due to material present within the cartilage matrix which selectively inhibits the action of collagenase.

The anti-invasion factor of the present invention inhibits the action of collagenase. It is believed that its collagenase-inhibiting characteristic is involved both in its activity as a tissue invasion inhibitor and its activity as an inhibitor of bone resorption. While applicant does not intend the scope of his invention to be delimited, restricted or otherwise bound by theory, it is believed that the collagenase elaborated by the osteoclasts involved in bone resorption is regulated or inhibited by the AIF of the present invention.

Those skilled in the art will immediately recognize the potential applicability of the present invention to various bone resorption processes, with the aim of regulating, controlling or stopping the resorptive process.

Various of the features of the present invention are set forth in the following claims.

What is claimed is:

1. A method for regulating bone resorption comprising exposing the bone to an effective amount of a composition of matter obtained from avascular or poorly vascularized tissue by extracting the tissue with an aqueous extraction medium which includes a solute which does not irreversibly denature the proteinaceous matter to be extracted, separating the resultant aqueous extract from the tissue, recovering from the aqueous extract substances having a molecular weight below about 50,000, and treating the fraction of aqueous extract having a molecular weight below about 50,000 to remove salts therefrom.

2. The method of claim 1 wherein the tissue comprises cartilage.

3. The method of claim 1 wherein the tissue comprises blood vessel walls.

4. The method of claim 1 wherein the tissue comprises cornea.

5. The method of claim 1 wherein the tissue comprises dentin.

6. The method of claim 1 wherein the tissue comprises heart valve.

7. The method of claim 1 wherein the tissue comprises vitreous.

8. The method of claim 1 wherein the tissue comprises lens.

9. The method of claim 1 wherein the tissue comprises synovial fluid.

10. The method of claim 1 wherein substances having a molecular weight between about 2,000 and 50,000 are recovered from the aqueous extract.

* * * * *